United States Statutory Invention Registration [19]

[11] Reg. Number: H688

Sobataka et al. [43] Published: Oct. 3, 1989

[54] PROCESS FOR SURFACE MODIFICATION OF POLYETHYLENE TEREPHTHALATE FILM

[75] Inventors: Warren S. Sobataka, Circleville, Ohio; William R. Wolfe, Jr., Wilmington, Del.

[73] Assignee: E. I. Du Pont de Nemours and Company, Wilmington, Del.

[21] Appl. No.: 207,536

[22] Filed: Jun. 16, 1988

[51] Int. Cl.[4] ..... C07C 3/24; C08F 2/52
[52] U.S. Cl. ..... 204/165
[58] Field of Search ..... 204/165, 168

[56] References Cited

U.S. PATENT DOCUMENTS

| | | | |
|---|---|---|---|
| 3,853,657 | 12/1974 | Lawton | 204/165 |
| 4,024,038 | 5/1977 | Luc | 204/165 |
| 4,297,187 | 10/1981 | Deguchi et al. | 204/165 |
| 4,536,271 | 8/1985 | Collins | 204/165 |
| 4,594,262 | 6/1986 | Kreil et al. | 427/44 |

FOREIGN PATENT DOCUMENTS 2544324 10/1984 France .

*Primary Examiner*—John F. Terapane
*Assistant Examiner*—John M. Covert
*Attorney, Agent, or Firm*—David M. Shold

[57] ABSTRACT

An improved process for surface modification of polyethylene terephthalate film is provided, involving corona discharge treatment of the film in an atmosphere of nitrogen containing up to about 350 ppm oxygen, and optionally a small amount of acetone vapor. Films so treated exhibit improved surface properties.

12 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

PROCESS FOR SURFACE MODIFICATION OF POLYETHYLENE TEREPHTHALATE FILM

BACKGROUND OF THE INVENTION

This invention relates to an improved process for surface modification of polyethylene terephthalate (PET) film involving corona discharge.

The treatment of films or other shaped articles made of PET using a corona discharge to improve their surface characteristics such as adhesive properties is well known. However, such treatment is often insufficient to achieve the desired improvements. Several attempts have therefore been made to improve the surface characteristics beyond those obtainable by simple corona discharge treatment.

U.S. Pat. No. 4,594,262, to Kreil et al., discloses a method for coating a polyester film base with a curable organic coating, by (1) continuously passing uncoated polyester film base through an inert atmosphere containing less than 100 ppm oxygen, while (2) exposing the film base to irradiation by an electron beam, to subject the film base to an absorbed dosage of at least 1 Mrad, and (3) applying a curable organic coating to the surface of the polyester film. The polyester film, after step (2), is substantially more adherent to organic coatings than such film which has not been so treated, and this greater adherence lasts for prolonged periods during storage at room temperature in air.

French patent No. 2,544,324 discloses a process for increasing the adherence of the surface of a shaped product made of a polyester composition. This process consists of the application of a corona discharge to this surface, which is continuously moving between a discharge electrode and another, opposite electrode. An atmosphere containing oxygen in an amount not exceeding 20% by volume is projected onto the surface to which the corona discharge is applied.

SUMMARY OF THE INVENTION

This invention provides a process for treating a polyester film with a corona discharge in an apparatus comprising at least one electrode and a housing provided with a means for admitting a gas and substantially excluding ambient air, comprising the steps of:

(a) providing an atmosphere, within the housing, of nitrogen containing up to about 350 parts per million molecular oxygen;

(b) adjusting the energy density of the corona discharge to a value of about 90 to about 140 watts per square inch;

(c) continuously passing said film through said housing; and (d) exposing said film, within said housing provided with said nitrogen atmosphere, to said corona discharge, wherein the exposure of said film to said corona discharge is from about 2 to about 64 watt minutes of corona energy per square foot of film.

The present invention also provides film prepared by the above process.

DETAILED DESCRIPTION OF THE INVENTION

The present invention provides a process for treating a film or other shaped article of PET with a corona discharge under an atmosphere of nitrogen, in order to improve the adhesion characteristics of the film, by increasing the total adhesion and reducing the variability in the adhesion, when compared to corona treatment in an atmosphere of air.

The film which may be successfully treated using this process includes polyester film. Various types of polyester film may be used, but the preferred polyester is polyethylene terephthalate.

In order to attain the improvements of the present invention, it is necessary that the atmosphere overlaying the PET film in the region where the corona discharge treatment is being effected is replaced by an atmosphere containing nitrogen, from which oxygen has been substantially removed. An atmosphere of nitrogen containing no more than about 320 parts per million oxygen has been found to be suitable. Other materials may also be present in the nitrogen. For example, we have found that successful results may be obtained at low oxygen levels when acetone vapor is also present in the nitrogen, at levels up to saturation. But it is preferred that nitrogen, without any other added materials, be used.

Devices suitable for corona treatment of films are well known in the art, and are described, for example, in U.S. Pat. No. 3,133,193. Generally, a suitable configuration includes a grounded metal roll with an insulated cover, and an electrode mounted parallel to the cylinder axis of the roll. The film passes over the insulated roll, and the corona is developed between the electrode and the film. The electrode gap, which is the distance between the electrode and the insulated roll cover should be about 30 to 100 mils, preferably about 40 mils. The corona discharge apparatus of this invention also includes a means for supplying nitrogen, and a means for maintaining the nitrogen atmosphere, excluding ambient air. Such a modified apparatus is also well known, and is illustrated, for example, in French Pat. Appl. No. 2,544,324.

The amount of energy applied to the film is important, in that a certain minimum amount is needed in order to achieve the desired improvements in surface properties of the film, and an upper limit is normally set by economic considerations. The energy applied is expressed as the power constant, which is traditionally in units of watt-minutes per square foot of film. The power constant is equal to the corona power, in watts, divided by the product of the film width and the line speed, in feet per minute. Suitable values for the power constant are about 2 to roughly 64 W-min/ft2 The upper limit is quite flexible. For economic reasons, a power constant of about 3 to about 10 are preferred, and most preferably near 3. At power constants much below 3, the benefits of this invention are less fully realized. A variety of apparatus and geometrical arrangement are possible to achieve this level of treatment. Some such parameters are further described in the following paragraphs.

The corona power required will vary with the size of the apparatus and the rate of treatment of film. A small, laboratory scale corona treater may be designed to treat a web of film 4 inches wide, at a rate of about 7 to 72 feet per minute. Such an apparatus may use a discharge of about 50 to about 150 watts in order to obtain a suitable power constant. Larger commercial corona treaters require correspondingly more power. For example, treating a 6 foot wide film web at a line speed of 500 or 1000 feet per minute, the required corona power is 9 or 18 kW, respectively, to obtain a power constant of 3 W-min/ft$^2$. The frequency may be typically about 18-40 kHz. A laboratory scale treater may have an electrode area of about 0.36 to about 2.25 square inches, so that the electrode energy density is typically in the range of about 44 to about 150 watts/in$^2$ A commercial unit would have a correspondingly larger electrode area.

We have found that the improvement of this invention can be achieved using a variety of combinations of electrode energy density and power constant. These two factors are interrelated. At power constants much below 3 watt min/sq. ft., and at electrode energy densities much below about 100 watts/sq. in., the absolute values of adhesion diminish, although the samples corona treated in a nitrogen atmosphere may continue to be superior to those corona treated in air. Thus this invention is particularly useful when the electrode energy density is at least about 90, or preferably at least about 100 watts/sq. in., and the power constant is at least about 2, or preferably at least about 3 watt minutes/square foot. Film width, speed, and other parameters can be adjusted by the person skilled in the art to achieve these values.

The improvements obtained by treating films of PET according to this invention are illustrated in the following nonlimiting examples:

EXAMPLES

Example 1

A laboratory scale corona treater is located in a scrap vacuum evaporator. The corona treater includes a 3.5 inch diameter grounded corona roll with a fluoropolymer cover. A 4 inch long electrode, having an area of 2.25 square inches, is mounted parallel to the cylinder axis of the roll, to provide an electrode gap of 40 mils. The apparatus is provided with a controlled nitrogen atmosphere by evacuating to about 28 inches of Hg vacuum, then returning the unit to atmospheric pressure by back filling with nitrogen. This procedure is repeated two more times. After the third filling, the unit is purged with nitrogen until an oxygen concentration of less than 10 ppm is reached, as measured using a "Teledyne" oxygen meter. (During the treatment the oxygen concentration drops to 3.5 ppm.) A corona is generated by supplying 150 watts at 22.5 kHz to the electrode from a solid-state corona power supply. A sample of 0.5 mil PET film is passed through the corona using a D. C. powered motor, at 7 ft/min, as measured by a tachometer. These conditions correspond to a power constant of 64 watt min/sq. ft. and an electrode energy density of about 66 watts/sq. in.

After treatment, the film is removed from the apparatus and coated with india ink by spreading the ink across the film with a handproofer until the film is covered. The ink, after drying, cannot be removed using "Scotch" brand 810 adhesive tape. This test indicates satisfactory adhesion.

Example 2

A series of experiments is run similar to that of Example 1. The line speed of the corona treater is 32.5 ft/min. The 0.5 mil PET film is corona treated in an air atmosphere, a nitrogen atmosphere, or a nitrogen atmosphere saturated with acetone (designated as "Air,""Nitrogen," and "Acetone" in the Tables below). The oxygen concentration in the treater is 4.5 ppm when treating with nitrogen and 3.4 ppm when treating with acetone/nitrogen. Using an electrode area of 1.06 sq. in., 100 watts of corona energy at 21.4 kHz is applied during treatment. These conditions give a power constant of 9.2 watt min/sq. ft. and an electrode energy density of 94 watts/sq. in.

The film is evaluated by an ink adhesion test similar to that in Example 1. In this test, an amount of ink is applied which is sufficient to cover the film surface. Two types of ink are typically used, Converters Ink Co. Ink #P-73741 ("white") and Ink #P-73745 ("red"). These inks are diluted with 90% ethanol/10% propyl acetate to a viscosity of about 22 seconds as measured in a Zahn viscosimeter #2 cup. The ink sample is drawn across the film surface using a "Parmarco Hand Proofer" with a #165 steel roll, before significant solvent loss due to evaporation can occur. The inked film is dried in an oven at about 85 C for about 10 seconds, cooled, and allowed to age for at least 5 minutes. A 6 inch minimum length of adhesive tape ("Scotch"#610 or equivalent) is applied to the ink and pressed down with a roller. The tape is then peeled back at an angle of a little less than 180°. A slow steady pull is used for the first half of the contact area ("Slow"), followed by a rapid, "snapping" removal rate for the remainder ("Fast"). The results are reported numerically as follows:

10: no ink removed by the tape

9: 90% of ink remaining, 10% removed etc.

The results of the ink adhesion test are shown in Table I, and are compared with a commercial grade of PET film which is corona treated in air, a product from E. I. du Pont de Nemours and Co, Inc.

TABLE I

| | Ink: White | Red | Red on White |
|---|---|---|---|
| | Rate: slow/fast | slow/fast | slow/fast |
| System: | | | |
| Nitrogen | 9/9 | 9.5/9 | 10/10 |
| Acetone | 8.6/5.3 | 7/6 | 10/9 |
| Air | 6/5 | 8/6.5 | 3/3 |
| Commercial | 8/5 | — | 4/5 |

Example 3

Example 2 is repeated, but at a line speed of 50 ft/min. These conditions give a power constant of 6.0 watt min/sq. ft. and an electrode energy density of 94 watts/sq. in. The results are shown in Table II, wherein the heading are the same as in Table I.

TABLE II

| | | | |
|---|---|---|---|
| Nitrogen | 10/10 | 10/10 | 10/10 |
| Acetone | 10/9 | 10/10 | 10/9 |
| Air | 5/7.7 | 10/10 | 4/9 |

Example 4

PET film is treated as in Example 2, at a line speed of 71–73 ft/min. The power constant is thus somewhat lower than in Examples 2 and 3, being 4.2 watt min/sq. ft. Adhesion values are shown in Table III, wherein the headings are the same as in Table I. This increase in line speed results in a decrease in the adhesion values.

TABLE III

| | | | |
|---|---|---|---|
| Nitrogen | 10/2 | 9/5 | 9/2 |
| Acetone | 10/2 | 0/0 | 10/6 |
| Air | 6/7 | 10/0 | 2/6.5 |

Example 5

PET film is treated as in Example 4, with a line speed of 71–73 ft/min, an electrode area of 0.531 sq. in., and 75 watts electrode power. These conditions give an electrode energy density of 140 watts/sq. in. and a power constant of 3.1 watt min/sq. ft. Duplicate measurements are made. A marked increase in adhesion is obtained for nitrogen and air treated film when compared with values of Example 4. The increase adhesion of this example is obtained at a higher electrode energy but a lower power constant than Example 4. The results are shown in the Table IV.

TABLE IV

| | | | |
|---|---|---|---|
| Nitrogen | 10/10 | 10/10 | 10/10 |
| Acetone | 0/0 | 10/9.7 | 7.3/8.7 |
| Air | 10/9.7 | 10/10 | 9/9.7 |

Example 6

PET film is corona treated in the presence of nitrogen under the conditions of Example 5. However, the oxygen content is varied as shown in Table V. Using these conditions, excellent adhesion results using oxygen concentrations of up to 350 ppm.

TABLE V

| | | | |
|---|---|---|---|
| 5 ppm $O_2$ | 10/10 | 10/10 | 10/10 |
| 175 ppm | 10/10 | 10/10 | 10/10 |
| 350 ppm | 10/10 | 10/10 | 10/10 |

Example 7

PET film is corona treated as in Example 5 except the electrode energy density is 125 watts/sq. in. Adhesion values are shown in Table VI.

TABLE VI

| | | | |
|---|---|---|---|
| Nitrogen | 10/10 | 10/10 | 10/9.5 |
| Acetone | 0/0 | 10/10 | 0/3.5 |
| Air | 1/8 | 10/10 | 3/8 |

Example 8

Pet film is corona treated as in Example 5 except the electrode energy density is 110 watts/sq. in. Adhesion values are shown in table VII.

TABLE VII

| | | | |
|---|---|---|---|
| Nitrogen | 9.5/10 | 10/10 | 9/10 |
| Acetone | 0.5/0.5 | 10/10 | 0/3 |
| Air | 6.5/5 | 10/10 | 5.5/10 |

Example 9

Pet film is corona treated as in Example 5 except the electrode energy density is 100 watts/sq. in., the total electrode energy is 50 watts, and the line speed is 48.5 ft/min. The power constant is 3.1 watt min/sq. ft. as in Example 5. Table VIII shows that the results are marginal for corona treatment in a nitrogen atmosphere under these conditions.

TABLE VIII

| | | | |
|---|---|---|---|
| Nitrogen | 9.2/7.4 | 9.4/9.6 | 6.2/10 |
| Acetone | 0/0 | 10/10 | 0/5.2 |
| Air | 6.2/8.2 | 10/10 | 2.8/8.6 |

Example 10

Pet film is corona treated as in Example 5, with an energy density of 140 watts/sq. in., except the power constant is 2.1 watt/sq. ft. and the electrode energy is 50 watts. The results in Table IX indicate that the adhesion properties are not as good as those obtained at higher power constants, but the samples run under nitrogen continue to give improved results compared to air.

We claim:

TABLE IX

| | | | |
|---|---|---|---|
| Nitrogen | 3/8.5 | 10/10 | 1.5/9 |
| Acetone | 0/0 | 10/10 | 0/1.5 |
| Air | 1.5/3.5 | 10/10 | 0/6.5 |

1. A process for treating a polyester film with a corona discharge in an apparatus comprising at least one electrode and a housing provided with a means for admitting a gas and substantially excluding ambient air, comprising the steps of:

(a) providing an atmosphere, within the housing, of nitrogen containing up to about 350 parts per million molecular oxygen;

(b) adjusting the energy density of the corona discharge to a value of about 90 to about 140 watts per square inch;

(c) continuously passing said film through said housing; and (d) exposing said film, within said housing provided with said nitrogen atmosphere, to said corona discharge, wherein the exposure of said film to said corona discharge is from about 2 to about 64 watt minutes of corona energy per square foot of film.

2. The process of claim 1 wherein the atmosphere of nitrogen contains up to about 175 parts per million oxygen.

3. The process of claim 2 wherein the atmosphere of nitrogen contains up to about 5 parts per million oxygen.

4. The process of claim 3 wherein the film is exposed to about 3 to about 10 watts minutes of corona discharge per square foot of film.

5. The process of claim 4 wherein the energy density of the corona discharge is about 100 to about 140 watts per square inch.

6. The process of claim 5 wherein the width of said film is about 6 feet and the speed of said film through said housing is about 500 to about 1200 feet per minute.

7. The process of claim 5 wherein the film is polyethylene terephthalate.

8. The process of claim claim 3 wherein the nitrogen contains acetone vapor.

9. A film prepared by the process of claim 1.

10. A film prepared by the process of claim 4.

11. A film prepared by the process of claim 6.

12. A film prepared by the process of claim 7.

* * * * *